(12) United States Patent
Otera

(10) Patent No.: US 8,891,085 B2
(45) Date of Patent: Nov. 18, 2014

(54) GAS ANALYZER

(71) Applicant: Shimadzu Corporation, Kyoto-shi, Kyoto (JP)

(72) Inventor: Fumiaki Otera, Kyoto (JP)

(73) Assignee: Shimadzu Corporation, Kyoto-shi (JP)

( * ) Notice: Subject to any disclaimer, the term of this patent is extended or adjusted under 35 U.S.C. 154(b) by 267 days.

(21) Appl. No.: 13/667,339

(22) Filed: Nov. 2, 2012

(65) Prior Publication Data

US 2014/0125967 A1    May 8, 2014

(51) Int. Cl.
*G01N 21/61* (2006.01)
(52) U.S. Cl.
USPC .......................................... 356/437; 356/326
(58) Field of Classification Search
USPC .......... 356/432–440, 301, 326; 250/343, 345, 250/339.11
See application file for complete search history.

(56) References Cited

U.S. PATENT DOCUMENTS

| 5,880,850 | A | 3/1999 | McAndrew et al. | |
|---|---|---|---|---|
| 6,442,736 | B1 | 8/2002 | Girard et al. | |
| 8,149,407 | B1 * | 4/2012 | Rao | 356/437 |
| 8,390,813 | B2 * | 3/2013 | Clegg et al. | 356/437 |
| 2010/0242572 | A1 * | 9/2010 | Yu | 73/24.02 |
| 2013/0321815 | A1 * | 12/2013 | Otera | 356/437 |
| 2014/0022542 | A1 * | 1/2014 | Otera | 356/300 |

FOREIGN PATENT DOCUMENTS

| JP | 5-99845 A | 4/1993 |
|---|---|---|
| JP | 2002-184767 A | 6/2002 |
| JP | 2004-361128 A | 12/2004 |
| JP | 2008-298635 A | 12/2008 |
| JP | 2009-192246 A | 8/2009 |

OTHER PUBLICATIONS

Japanese Office Action dated May 28, 2013, issued in corresponding Japanese Patent Application No. 2010-088545, w/ partial English translation.

* cited by examiner

*Primary Examiner* — Hoa Pham
(74) *Attorney, Agent, or Firm* — Westerman, Hattori, Daniels & Adrian, LLP

(57) ABSTRACT

A gas analyzer includes: a first signal processing section for synchronously detecting a light detection signal at a frequency being an integral multiple of a modulation frequency fa of a laser light, to detect a harmonic signal intensity Signal (v) by a harmonic synchronous detection method; a second signal processing section for capturing a light detection signal and cutting off a frequency component not smaller than the frequency fa to detect a light intensity signal I(v) at a specific light frequency absorbed by a component to be measured in a sample gas; and an operation section. The operation section includes a first operation means for calculating a density c of the component from the harmonic signal intensity Signal(v) and a reference light intensity signal $I_0(v)$ and a second operation means for calculating the density c from the light intensity signal I(v) and the reference light intensity signal $I_0(v)$.

9 Claims, 15 Drawing Sheets

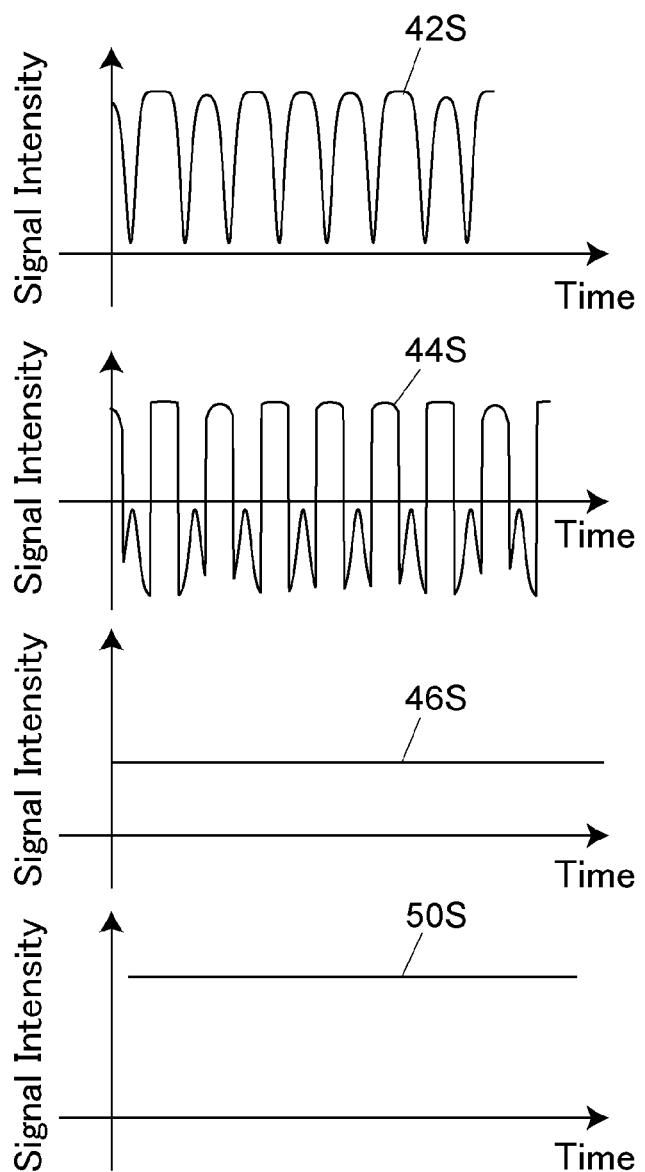

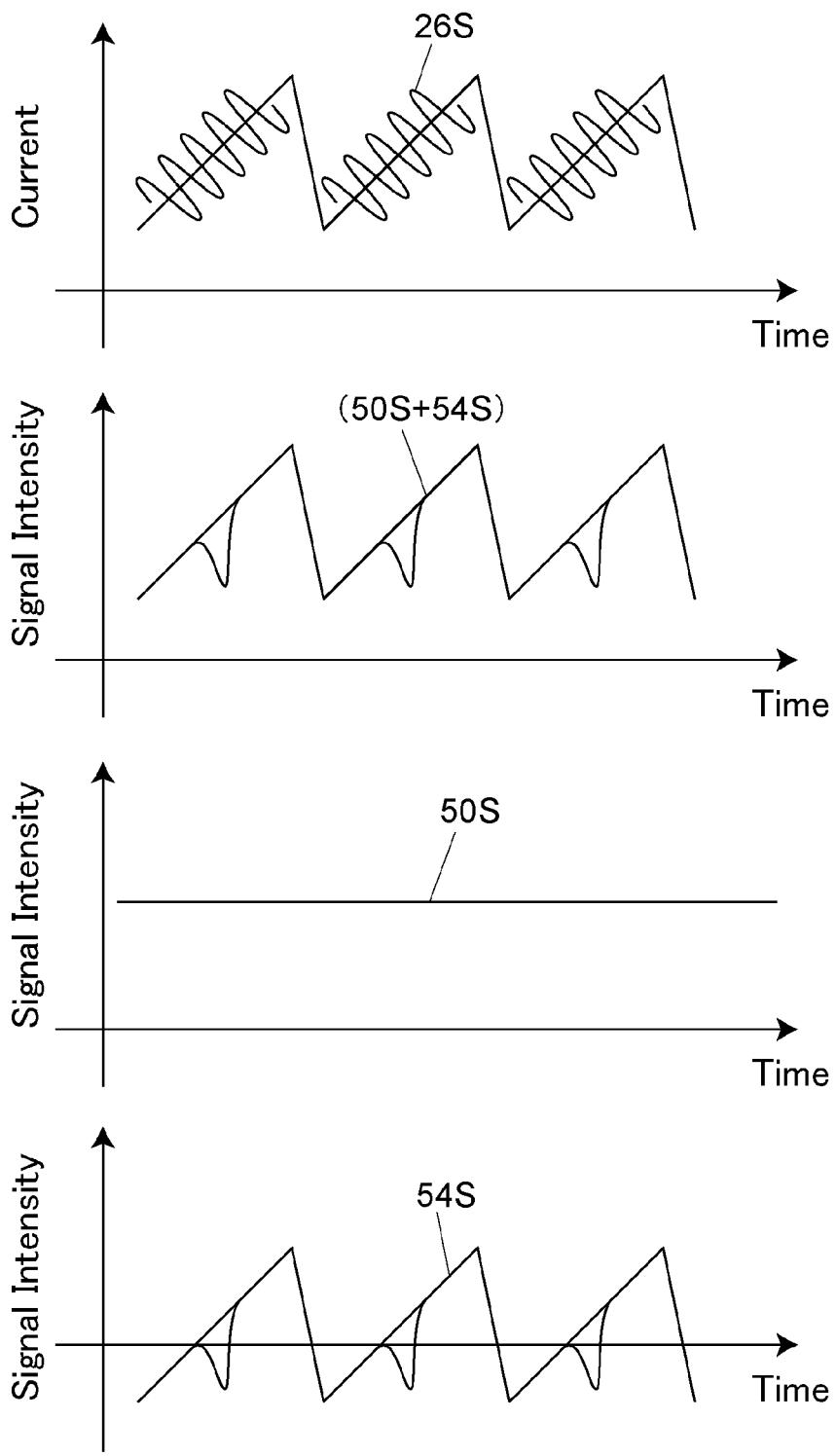

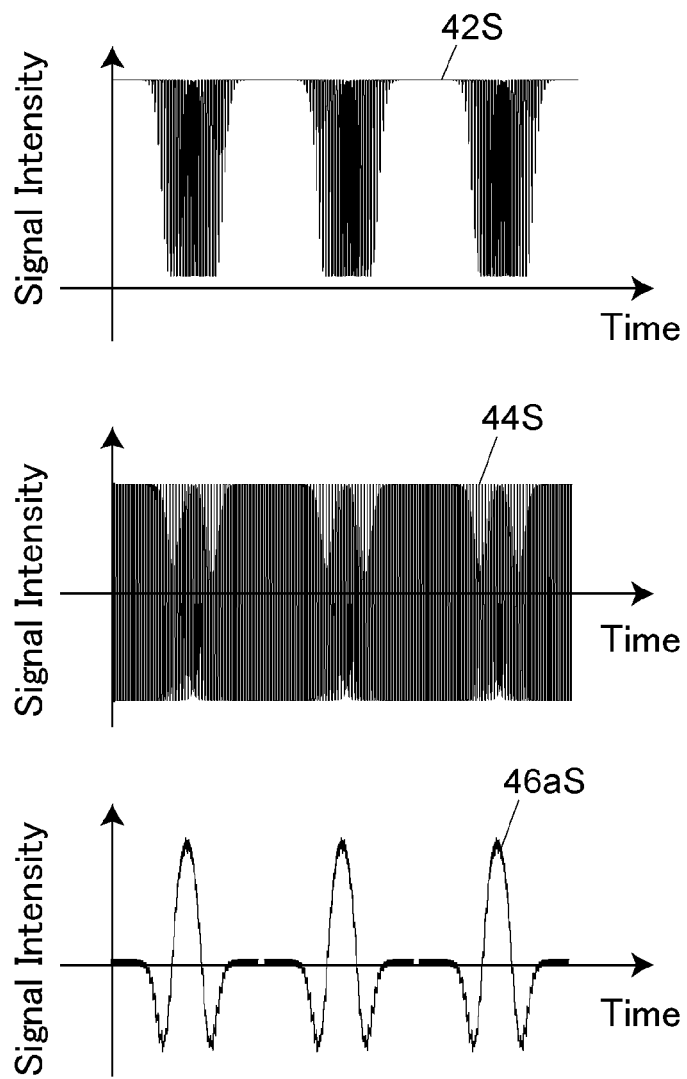

GAS ANALYZER

BACKGROUND OF THE INVENTION

1. Field of the Invention

The present invention relates to a gas analyzer for measuring a molecular number density of a component to be measured in a sample gas by means of absorption of laser gas.

2. Description of the Related Art

In recent years, as a method for measuring a molecular number density of a specific gas in a vapor, laser absorption spectroscopy by means of absorption of laser light has been proposed (e.g., Unexamined Japanese Patent Publication No. 5-099845). This method is to irradiate a sample cell, where a sample gas has been introduced, with laser light with a predetermined frequency and to analyze the transmitted laser light, to derive a molecular number density of a component to be measured in the sample gas from the degree of absorption in the component to be measured. This device is a non-contact type where a light receiving section as a sensor is not in contact with the sample gas, thereby having an advantage of being capable of measurement without disturbing a sample place and an advantage of having extremely short response time. In order to select a measurement frequency with respect to the component to be measured in the sample gas, a wavelength tunable laser is used as a light source of laser light.

Hereinafter, a general theory of infrared absorption spectroscopy using laser light will be described. It is to be noted that the case of measuring minute amounts of water-vapor molecular number densities in a nitrogen gas will here be taken as an example.

The relation between a detected light reception intensity of laser light and a water-vapor molecular number density is shown by Formula (1) from the following Lambert-Beer Law. $I_0(\nu)$ is a light intensity in the case of light without absorption by water molecules at a frequency $\nu$, and $I(\nu)$ is a transmitted light intensity at the frequency $\nu$. Further, $c$ is a molecular number density of the water molecules, $l$ is a length of an optical path passing through the component to be measured, $S$ is an absorption line intensity at the predetermined frequency $\nu$, and $K(\nu)$ is an absorption characteristic function.

$$\ln\left(\frac{I_0(\nu)}{I(\nu)}\right) = c \times l \times S \times K(\nu) \tag{1}$$

When the sample gas is the atmospheric pressure, the absorption characteristic function $K(\nu)$ is expressed by Formula (2) in accordance with a Lorentz profile. $\gamma_L$ is a half width of an absorption spectrum, and decided in accordance with type, temperature and pressure of the sample gas. $\nu_0$ is a center frequency of the absorption spectrum.

$$K(\nu) = \frac{\gamma_L}{\pi[(\nu - \nu_0)^2 + \gamma_L^2]} \tag{2}$$

Next Formula (3) is held from Formula (1) and Formula (2) above.

$$\ln\left(\frac{I_0(\nu)}{I(\nu)}\right) = c \times l \times S \times \left(\frac{\gamma_L}{\pi[(\nu - \nu_0)^2 + \gamma_L^2]}\right) \tag{3}$$

When a wavelength tunable laser is used, whose oscillating frequency width is far smaller than a line width of the absorption spectrum, such as a DFB (Distributed Feedback) semiconductor laser, it is possible to perform measurement at each frequency $\nu$ without separately using a spectrometer.

An absorption intensity $I(\nu_0)$ at the center frequency $\nu_0$ is expressed in Formula (4) as $\nu = \nu_0$ in Formula (3).

$$\ln\left(\frac{I_0(\nu)}{I(\nu_0)}\right) = c \times l \times S \times \frac{1}{\pi \gamma_L} \tag{4}$$

Meanwhile, in infrared absorption by the water molecules in an extremely low total pressure region (high vacuum region where total pressure of the component to be measured is lower than 1 [Torr]), the absorption spectrum width is as small as the order of a few percent to a few tens of percent of expansion of the foregoing Lorentz profile. In this total pressure region, the absorption characteristic width is decided mainly by the Doppler effect. The absorption characteristic function $K(\nu)$ in this case is expressed by Formula (5) (Gaussian function) below. In Formula (5), $\gamma_{ED}$ is one called a Doppler width, which depends on a center frequency of the absorption spectrum, a molar weight and a temperature.

$$K(\nu) = \frac{1}{\gamma_{ED}\sqrt{\pi}} \times \frac{1}{\exp\left(\frac{\nu - \nu_0}{\gamma_{ED}}\right)^2} \tag{5}$$

In this case, Formula (6) below is held from Formula (1) and Formula (5), and $\nu = \nu_0$ is made to be held in Formula (6), whereby the absorption intensity $I(\nu_0)$ at the center frequency $\nu_0$ can be expressed by Formula (7) below.

$$\ln\left(\frac{I_0(\nu)}{I(\nu)}\right) = c \times l \times S \times \frac{1}{\gamma_{ED}\sqrt{\pi}} \times \frac{1}{\exp\left(\frac{\nu - \nu_0}{\gamma_{ED}}\right)^2} \tag{6}$$

$$\ln\left(\frac{I_0(\nu_0)}{I(\nu_0)}\right) = c \times l \times S \times \frac{1}{\gamma_{ED}\sqrt{\pi}} \tag{7}$$

In general infrared absorption spectroscopy using laser light, the absorbed light intensities $I_0(\nu_0)$ and $I(\nu_0)$ at the center of the absorption line are measured from Formula (4) or (7) above, to calculate an amount of the component to be measured in the sample gas.

Further, as a gas analyzing method using laser light, there is a detection method referred to as light absorption spectroscopy (hereinafter referred to as a harmonic synchronous detection method) performed by means of harmonic detection which detects second harmonic component in an absorption spectrum waveform, and the like (e.g. see U.S. Pat. No. 5,880,850 and Unexamined Japanese Patent Publication No. 2002-184767). The harmonic synchronous detection method is known especially as a high sensitive detection technique among the infrared absorption spectroscopy, and is a detection method which is effective when a light absorption amount of the component to be measured is minute.

The harmonic synchronous detection method will be described based on Reference 1. In the case of the light absorption amount of the component to be measured being minute as in the case of harmonic detection being required, Formula (1) as the Lambert-Beer Law can be approximated by the following Formula (8).

$$\ln\left(\frac{I_0(v)}{I(v)}\right) \approx \frac{I_0(v) - I(v)}{I_0(v)} = c \times l \times S \times K(v) \quad (8)$$

Performing the harmonic detection requires modulating a frequency of light, with which the component to be measured is irradiated. When a modulation amplitude of a sine-wave signal for modulating a frequency is a and the frequency is ω, the frequency of light at time t is defined by the following Formula (9).

$$v_{mod}(t) = v + a\cos \omega t \quad (9)$$

In second harmonic detection, a signal component corresponding to a twofold frequency 2ω is extracted by synchronous detection out of detection signals from the light receiving section. When the light absorption amount is minute, the second harmonic detection signal intensity Signal(v) at the frequency v has a relation as in the following Formula (10). Hence a relation of the following Formula (11) is obtained from Formula (8). In Formula (11), const is a proportional constant, and changes in accordance with sensitivities of a detector and a harmonic synchronous detection circuit. A method for deciding this proportional constant const is to previously measure a gas with a known molecular number density, such as a gas whose molecular number density has been calculated by measurement based on Formula (1) above, thereby to decide the constant $$\text{Signal}(v) \propto (I_0(v) - I(v)) \quad (10)$$

$$\frac{\text{Signal}(v)}{I_0(v)} = \text{const} \times c \times l \times S \times \int_{-\pi}^{\pi} K(v + a\cos\theta)\cos(2\theta)\,d\theta \quad (11)$$

Although the harmonic synchronous detection method is highly sensitive, precise measurement is possible only on a condition where the approximation of Formula (8) above is held. Therefore, a precise detection result can be obtained when the component to be measured is one with a low molecular number density, whereas a precise detection result cannot be obtained when the component to be measured is one with a high molecular number density.

Also in the laser absorption spectroscopy, a method (hereinafter referred to as direct absorption spectrometry) for directly measuring $I_0(v_0)$ and $I(v_0)$ and obtaining a molecular number density of a component to be measured from Formula (4) or (7) is used, for example, for measuring a sample containing moisture with a relatively high molecular number density such as a moisture molecular number density in an aerial environment, whereas the harmonic synchronous detection method is used in such an area as measurement of minute amounts of moisture molecular number densities in a particular gas for use in a semiconductor manufacturing line. Further, since detection circuits are configured in different manners in the above two measuring methods, the respective measuring devices are configured as separate ones, and no measuring device usable for the both measuring methods exists.

Therefore, a precise measurement result cannot be obtained either in a case where the molecular number density of the component to be measured abruptly decreases while measurement is performed with the device using the direct absorption spectrometry or a case where, on the contrary, the molecular number density of the component to be measured abruptly increases while measurement is performed with the measurement device using the harmonic synchronous detection method.

SUMMARY OF THE INVENTION

An object of the present invention is to provide a gas analyzer allowing wide dynamic range measurement of a molecular number density of a component to be measured in a sample gas, while allowing continuous measurement without suspending the measurement for switching measurement modes even when the molecular number density abruptly changes.

A gas analyzer according to the present invention includes: a sample cell that allows a sample gas to flow therethrough; a laser irradiation section that irradiates the sample cell with laser light with a specific light frequency which is absorbed by a component to be measured in the sample gas; a light source driving section that applies a drive current for generating the laser light to the laser irradiation section; a modulation section that modulates the drive current applied from the light source driving section to the laser irradiation section with a modulation frequency of a first frequency fa; a light receiving section that receives the laser light having passed through the inside of the sample cell; a first signal processing section that synchronously detects a light detection signal of the light receiving section at a frequency being an integral multiple of the modulation frequency, to detect a harmonic signal intensity Signal(v) by a harmonic synchronous detection method; a second signal processing section that captures a light detection signal of the light receiving section not through the first signal processing section, and cuts off a frequency component not smaller than the first frequency fa by means of a frequency filter, to detect a light intensity signal I(v) at the specific light frequency; and an operation section that captures a harmonic signal intensity Signal(v) detected in the first signal processing section and the light intensity signal I(v) detected in the second signal processing section, to calculate a molecular number density c of the component to be measured in the sample gas.

The operation section includes a first operation means that calculates the molecular number density c of the component to be measured in the sample gas from the harmonic signal intensity Signal(v) and a reference light intensity signal $I_0(v)$, the reference light intensity signal being $I_0(v)$ when the laser light is not absorbed by the component to be measured at the specific light frequency, and a second operation means that calculates the molecular number density c of the component to be measured in the sample gas from the light intensity signal I(v) and the reference light intensity signal $I_0(v)$ by direct absorption spectrometry.

In the present invention, the operating section constantly captures a signal extracted in the first signal processing section and a signal extracted in the second signal processing section, and in accordance with a molecular number density of the component to be measured, specifically a signal intensity at a specific light frequency, more preferably a center frequency, of an absorption line of the component to be measured, the operation section selects either the molecular number density of the component to be measured, obtained by the harmonic synchronous detection method (first operation means), or the molecular number density of the component to be measured, obtained by the direct absorption spectrometry (second operation means). As thusly described, the harmonic synchronous detection method has high sensitivity, but linearity inconsistencies occur when the molecular number density is high. On the other hand, as for the direct absorption spectrometry, although its sensitivity is low as compared with that of the harmonic synchronous detection method, it can measure even a high molecular number density. The gas analyzer according to the present invention performs the above two measurement methods by use of the same laser control system, to parallelly extract a signal for use in the harmonic synchronous detection method and a signal for use in the direct absorption spectrometry from onetime light reception signal, and adopt, based on those signals, a molecular number density of the component to be measured which was obtained by appropriate measurement unit with respect to the molecular number densities of the component to be measured. This can compensate shortcomings of the two detection methods, to allow measurement in a wide range of the molecular number density, as well as allowing continuous measurement.

The operation section may simultaneously output measurement results obtained by the two operation means, and may be provided with switching means, to automatically select more accurate one in accordance with the molecular number density of the component to be measured in the sample. Such switching means determines from the light intensity signal $I(v)$ and the reference light intensity signal $I_0(v)$ as to whether the molecular number density of the component to be measured in the sample is a low molecular number density which is suitable for measurement by the harmonic synchronous detection method, or a molecular number density which is higher than the above molecular number density, and thus, suitable for measurement by the direct absorption spectrometry, and switches an output so as to output the molecular number density c calculated by the first operation means at the time of obtaining a determination result that it is the molecular number density suitable for the measurement by the harmonic synchronous detection method, and output the molecular number density c calculated by the second operation means at the time of obtaining a determination result that it is the molecular number density suitable for the measurement by the direct absorption spectrum.

A first aspect of the switching means is a unit capable of determining whether approximation in Formula (8) is held, and any units may be used so long as being unit capable of making such a determination. Specifically, either a value of $\ln(I_0(v)/I(v))$ or $(I_0(v)-I(v))/I_0(v)$ is constantly measured, to obtain a determination result that the molecular number density is a low molecular number density suitable for the measurement by the harmonic synchronous detection method at the time of the above measured value being not higher than a previously set threshold value, and to obtain a determination result that the molecular number density is a molecular number density suitable for the measurement by the direct absorption spectrum at the time of the above difference being larger than the set ratio.

A second aspect of the switching means is a unit using a difference $I_0(v)-I(v)$ between the reference light intensity signal $I_0(v)$ and the light intensity signal $I(v)$. Specifically, a determination result that the molecular number density is a molecular number density suitable for the measurement by the harmonic synchronous detection method is obtained at the time of the difference $I_0(v)-I(v)$ being smaller than a previously set threshold value, and a determination result that the molecular number density is a molecular number density suitable for the measurement by the direct absorption spectrum is obtained at the time of the above difference being larger than the set value. What is to be a set value for determination is decided in accordance with a measuring device.

Examples of a first aspect of the light source driving section may include one which sets a drive current to be applied to the laser irradiation section such that a light frequency of laser light applied from the laser irradiation section becomes a specific light frequency in an absorption range of the component to be measured, to fix the light frequency of laser light. In this case, it is necessary to previously perform separate measurement of the reference light intensity signal $I_0(v)$ at the time of no absorption of laser light by the component to be measured at the specific light frequency, and hence the operation section is provided with a reference light intensity signal $I_0(v)$ holding section that holds the reference light intensity signal $I_0(v)$. Then, a value of the reference light intensity signal $I_0(v)$ held in the reference light intensity signal $I_0(v)$ holding section is used as the reference light intensity signal $I_0(v)$ by the first operation means and the second operation means.

The most preferable one as the specific light frequency of laser light which is in the absorption range of the component to be measured is a center frequency ($v_0$) of the absorption line of the component to be measured. In that case, absorption becomes the largest, thereby allowing measurement with the most favorable S/N (signal to noise) ratio. Since the light source driving section needs to strictly control a drive current for driving the laser irradiation section in order to set the light frequency of laser light to the center frequency ($v_0$) of the absorption line of the component to be measured, a light source driving section with good performance is required. Even when it is difficult to precisely set the light frequency of laser light to the center frequency ($v_0$) of the absorption line of the component to be measured, the expected object of the present invention can be achieved so long as a decrease in S/N ratio is in an acceptable range. For this reason, the present invention provided with the first aspect of the light source driving section includes not only a case where the light frequency of laser light is set to the center frequency ($v_0$) of the absorption line of the component to be measured, but also a case where the light frequency is set to a light frequency off the center frequency ($v_0$) within the absorption range.

A second aspect of the light source driving section is one which does not fix the light frequency of laser light to the specific light frequency of the absorption line of the component to be measured. In this case, a laser wavelength scanning current generating section is provided which changes a laser drive current to be applied to the laser irradiation section such that the laser irradiation section oscillates even laser light with such a light frequency as not to be absorbed by the component to be measured. Then, the second signal processing section is provided with a portion which measures a transmitted light intensity at such a light frequency so as not to be absorbed by the component to be measured at the time when the laser wavelength scanning current generating section oscillates the laser light with such a light frequency so as not to be absorbed, to approximately calculate from a result of the measurement the reference light intensity signal $I_0(v)$ at a specific light frequency corresponding to the case of no absorption of light by the component to be measured. In this case, setting the light frequency of laser light to the center frequency ($v_0$) of the absorption line of the component to be measured is not necessary, thereby alleviating the requirement for performance of the light source driving section. Further, the reference light intensity signal $I_0(v)$ can also be obtained in the second signal processing section, thereby eliminating the need for previously measuring the reference light intensity signal $I_0(v)$.

A preferable example of the laser wavelength scanning current generating section is one which generates a sawtooth wave with a cycle of a second frequency fb that is lower than the first frequency fa.

Even in the case of providing the light source driving section of the first aspect which fixes the light frequency of laser light applied from the laser irradiation section, as an aspect for allowing the reference light intensity signal $I_0(v)$ to be simultaneously detected, a beam splitter is arranged between the sample cell and the laser irradiation section, and laser light emitted from the laser irradiation section is split by the beam splitter into laser light to be incident into the sample cell and laser light not to be incident into the sample cell. Then, a reference light receiving section is further provided which receives laser light that is the one split by the beam splitter and not incident into the sample cell. In that case, the second signal processing section cuts off a component not smaller than the first frequency fa component in a detection signal detected by the reference light receiving section, by the frequency filter, and detects a light intensity at the specific light frequency which has appeared after the above process, to regard it as the reference light intensity signal $I_0(v)$ at the specific light frequency which corresponds to the case of no absorption of light by the component to be measured.

The harmonic synchronous detection method has high sensitivity, but linearity inconsistencies occur when the molecular number density is high. On the other hand, the direct absorption spectrometry relatively has low sensitivity, but can perform measurement even with a high molecular number density. The gas analyzer according to the present invention performs the above two measurement methods by use of the same laser control system, to perform parallel measurement from onetime light reception signal, thereby making it possible to compensate shortcomings of the two detection methods, expand the range of the molecular number density to be measured, and hold measurement continuity.

In the present invention, the type of the specific gas as the object to be measured is not particularly specified, but the invention is effective to a gas with a molecular number density having a large change, and hence it is effective for measurements of a molecular number density of moisture in a gas to be measured.

BRIEF DESCRIPTION OF THE DRAWINGS

FIG. 2C is a waveform diagram showing a signal in FIG. 2A;

FIGS. 4C to 4F are waveform diagrams showing signals in FIG. 4A;

DETAILED DESCRIPTION OF THE INVENTION

Example 1

A first example of the present invention will be described using FIGS. 1, 2A and 2B. A gas analyzer of the present example is a moisture measuring device for measuring a molecular number density of moisture in a component to be measured.

Figure 1:
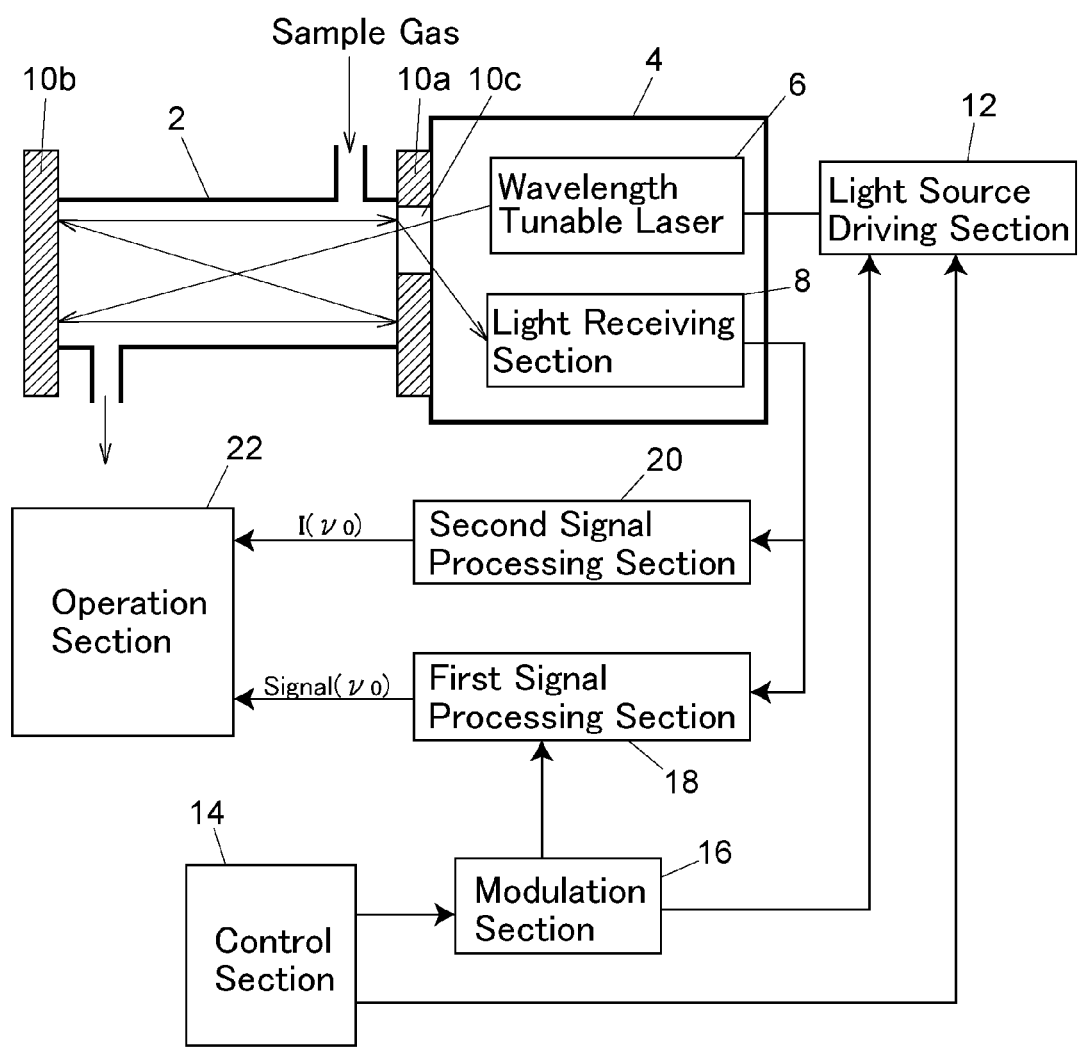
FIG. 1 is a schematic constitutional view showing a first example.

As shown in FIG. 1, the gas analyzer of the present example is provided with a sample cell 2 arranged in a substantially horizontal direction on a gas flow channel where a sample gas is allowed to flow downward from the above. Two mutually opposing reflectors 10a, 10b are provided on right and left opening ends of the sample cell 2. A part of the one reflector 10a is provided with a transparent window 10c which is, for example, made up of quartz so that only light is passable therethrough, and on the outside of the sample cell 2, with the reflector 10a sandwiched between the outside and the sample cell 2, an optical chamber 4 is mounted which has a substantially sealed structure and an atmosphere of substantially atmospheric pressure. Inside the optical chamber 4, a wavelength tunable laser 6 as a laser irradiation section is housed, and a light receiving section 8 is also housed. Inside the optical chamber 4, moisture as an interfering component is removed by means of a dehumidifying agent, a purge gas or the like, and thus reduced to such an extent that its molecular number is a negligible, and the chamber is sealed so as to be able to hold such a state, whereby the inside of the optical chamber 4 is in the state of the same atmospheric pressure as that of an external air so as to prevent entry of the external air. "A substantially sealed structure and an atmosphere of substantially atmospheric pressure" indicates a state where the moisture removed state inside the optical chamber 6 can be held.

It is to be noted that, although the transparent window 10c is used both for incidence and emission of laser light into and from the sample cell 2 in the example of FIG. 1, such a configuration may also be formed that transparent windows are separately provided for the incidence and emission.

The wavelength tunable laser 6 is, for example, a DFB laser and can generate laser light with a light frequency in a region covering a near-infrared region to a mid-infrared region. As the wavelength tunable laser 6, one other than the DFB laser can also be used. The wavelength tunable laser 6 is driven by a drive current from a light source driving section 12. The light source driving section 12 is one which gives a drive current to the wavelength tunable laser 6 such that laser light with the same frequency as the center frequency $v_0$ of the absorption line of the component to be measured is generated from the wavelength tunable laser 6. The light source driving section 12 is controlled by a control section 14. The drive current given from the light source driving section 12 to the wavelength tunable laser 6 is modulated by a modulation section 16 with a modulation frequency fa. The modulation section 16 will be described later.

It is configured such that, the inside of the sample cell 2 is irradiated with laser light from the wavelength tunable laser 6, and after the laser light is repeatedly reflected on the reflectors 10a, 10b several times, the laser light returns again to the optical chamber 4 from the transparent window 10c in the reflector 10a, to be incident on the light receiving section 8. Laser light is absorbed by a variety of components in the component to be measured when passing through the gas flow channel. The light receiving section 8 is provided with a photodiode as a light receiving element, and outputs as an electric signal an amount of light with each frequency, which has been incident on the photodiode. The signal outputted from the light receiving section 8 is subjected to predetermined processing in a first signal processing section 18 and a second signal processing section 20, and then captured by an operation section 22. The operation section 22 is realized by a computer.

In the first signal processing section 18, a detection signal from the light receiving section 8 is synchronously detected by regarding as a reference signal a clock signal with a frequency 2fa given from the modulation section 16, and a signal with the frequency 2fa is extracted. Naturally, the frequency 2fa means a twofold frequency of fa. An intensity of the signal extracted in the first signal processing section 18 is Signal($v_0$). Meanwhile, a signal with a frequency smaller than fa is extracted in the second signal processing section 20. An intensity of the signal extracted in the second signal processing section 20 is I($v_0$). The signal intensity Signal($v_0$) extracted in the first signal processing section 18 is a signal for performing measurement by the harmonic synchronous detection method, and the signal I($v_0$) extracted in the second signal processing section 20 is a signal for performing measurement by the direct absorption spectrometry.

The operation section 22 includes first operation means 23-1 that calculates a molecular number density of the component to be measured by the harmonic synchronous detection method based on the signal extracted by the first signal processing section 18, second operation means 23-2 that calculates a molecular number density of the component to be measured by the direct absorption spectrometry based on the signal extracted by the second signal processing section 20, a reference light intensity signal $I_0(v_0)$ holding section 23-3 made up of a memory to hold a signal intensity (reference light intensity signal) $I_0(v_0)$ in the case of no absorption of light by the component to be measured, and switching means 25 that decides which operation means is to be adopted, the operation means 23-1 or 23-2, in accordance with the molecular number density of the component to be measured, and the operation section 22 calculates the molecular number density of the component to be measured.

Figure 2A:
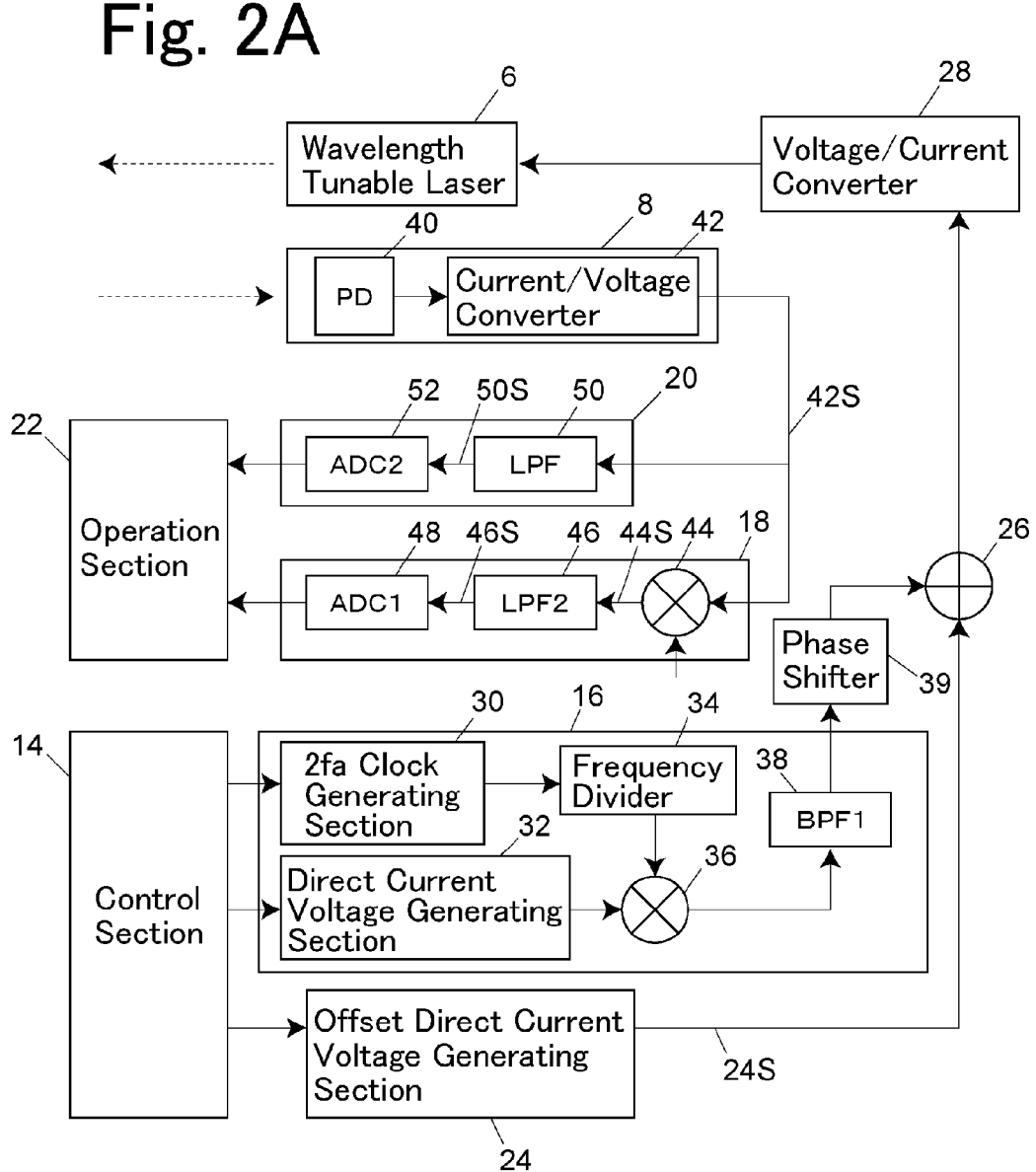
FIG. 2A is a block diagram showing an example of a configuration of a signal processing system according to the first example.
Figure 2B:
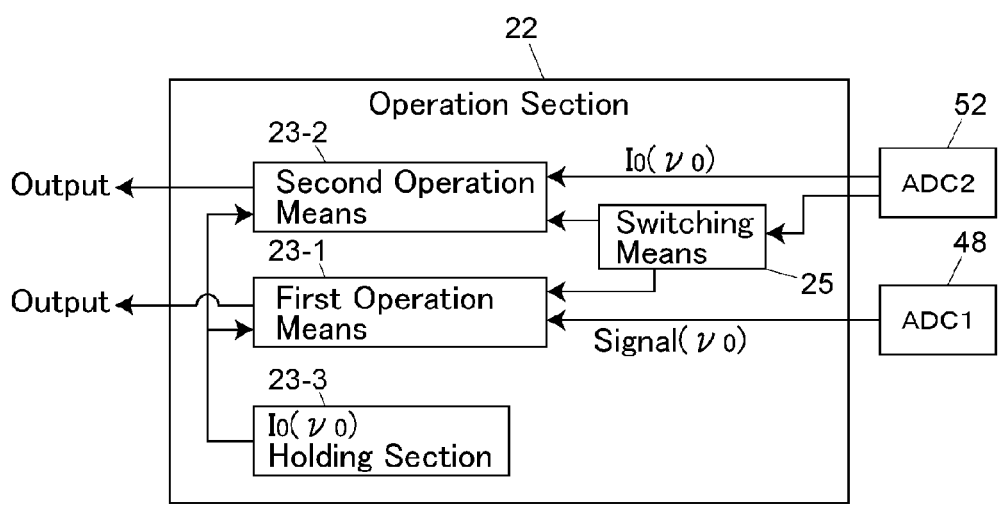
FIG. 2B is a block diagram showing an operation section according to the first example.

A detail of an example of the signal processing system of the present example will further be described using FIGS. 2A, 2B and 2C. In this example, the light source driving section 12 in FIG. 1 includes an adder 26, a voltage/current converter 28, and an offset direct current voltage generating section 24 for setting a light frequency of oscillated laser light to the center frequency $v_0$ of the absorption line of the component to be measured. The offset direct current voltage generating section 24 is one which generates a voltage signal 24S so as to lead emission of laser light with the center frequency of the absorption line of the component to be measured from the wavelength tunable laser 6, and is connected to the voltage/current converter 28 via the adder 26. The adder 26 is one which adds a modulation wave of the frequency fa from the modulation section 16 to the voltage signal 24S from the offset direct current voltage generating section 24, and the voltage signal 24S modulated at the frequency fa through the adder 26 is converted to a drive current in the voltage/current converter 28, and supplied to the wavelength tunable laser 6.

The modulation section 16 includes a frequency 2fa clock generating section 30 that generates a clock signal with the frequency 2fa, a direct current voltage generating section 32 that generates a direct current voltage for modulation amplitude control, a frequency divider 34 that converts the clock signal with the frequency 2fa to a clock with the frequency fa, a multiplier 36, and a band-pass filter (BPF1) 38 having a transmission region of the frequency fa±several hundreds of Hz for extracting a signal in the vicinity of the frequency fa. The direct current voltage for modulation amplitude control may be an arbitrary voltage, but when the direct current voltage is excessively large, an influence of a component with another light frequency strongly appears in the signal intensity I($v_0$) detected in the second signal processing section 20, which will be described later, thus making precise measurement impossible. In the modulation section 16, a clock signal with the frequency 2fa generated in the 2fa clock generating section 30 is converted to a clock signal with the frequency fa in the frequency divider 34, and the clock signal is multiplied by a direct current voltage for modulation amplitude control in the multiplier 36, which is then converted to a sine wave in the band-pass filter 38. The band-pass filter 38 is connected to the adder 26 via a phase shifter 39, and a signal voltage from the band-pass filter 38 is subjected to phase adjustment in the phase shifter 39, and then added to a voltage from the offset direct current voltage generating section 24.

Although the phase shifter 39 is arranged immediately after the modulation section 16 in the present example, it may, for example, perform phase adjustment before the first signal processing section 18 or the like, and the phase shifter 39 may be arranged in any place so long as harmonic synchronous detection can be performed.

The light receiving section 8 includes a photodiode (PD) 40 and a current/voltage converter 42. The photodiode 40 receives laser light, which reflects several times inside the sample cell 2 and is returned again into the optical chamber 4, and outputs an incident intensity as an electric signal. The current/voltage converter 42 converts the signal current from the photodiode 40 to a voltage, and outputs the voltage to the first signal processing section 18 and the second signal processing section 20.

The first signal processing section 18 includes a harmonic synchronous detection section 44 made up of a multiplier, a low-pass filter (LPF1) 46, and an A/D converter (ADC1) 48. As a signal waveform is shown in FIG. 2C, a detection signal 42S from the light receiving section 8 includes signals with the frequency 2fa and other harmonic components besides a signal with the frequency fa. In the harmonic synchronous detection section 44, a clock signal with the frequency 2fa from the 2fa clock generating section 30 of the modulation section 16 is multiplied, the half of the waveform of the frequency 2fa is reversed, and the frequency components other than the frequency 2fa are removed, to obtain a signal 44S. Passing of this signal 44S through a low-pass filter 46 leads to extraction of a peak signal intensity Signal($v_0$) 46 with a harmonic component of the frequency 2fa. The signal intensity Signal($v_0$) is converted to a digital signal in the A/D converter 48, and thereafter captured into the operation section 22.

The second signal processing section 20 includes a low-pass filter (LPF1) 50, and an A/D converter 52. The signal 42S from the light receiving section 8 is captured into the low-pass filter 50, and only a fluctuation component of an absorption peak passes therethrough as a signal 50S. The signal 50S is the signal intensity I($v_0$). It is appropriate that the low-pass filter 50, for example, have a time constant of the order of 0.1 second when a response rate is one second. That signal intensity I($v_0$) is converted to a digital signal in the A/D converter 52, and thereafter captured into the operation section 22.

As described above, the operation section 22 includes a first operation means 23-1 that calculates a molecular number density c of the component to be measured by the harmonic synchronous detection method based on the signal intensity Signal($v_0$) from the first signal processing section 18 by use of foregoing Formula (11), and a second operation means 23-2 which calculates a molecular number density c of the component to be measured by the direct absorption spectrometry based on the signal intensity I($v_0$) from the second signal processing section 20 by use of foregoing Formula (7). In the present example, the reference light intensity signal $I_0(v_0)$ in the case of no absorption of light by the component to be measured is previously measured and held in the reference light intensity signal $I_0(v_0)$ holding section 23-3 of the operation section 22.

$$\ln\left(\frac{I_0(v_0)}{I(v_0)}\right) = c \times l \times S \times \frac{1}{\gamma_{ED}\sqrt{\pi}} \quad (7)$$

$$\frac{\text{Signal}(v)}{I_0(v)} = const \times c \times l \times S \times \int_{-\pi}^{\pi} K(v + a\cos\theta)\cos(2\theta)\,d\theta \quad (11)$$

Figure 3:
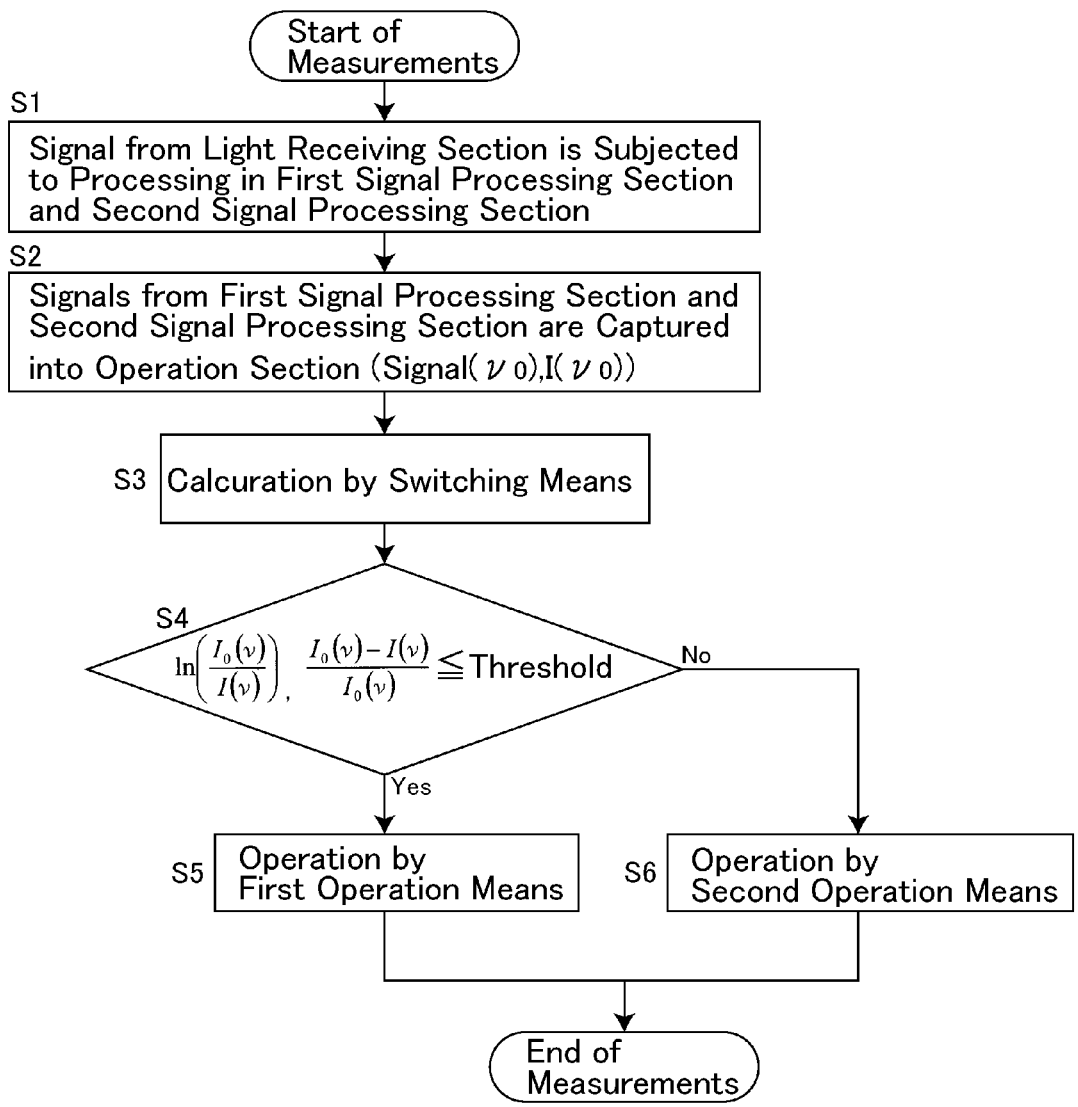
FIG. 3 is a flowchart showing a signal processing operation and an operation processing operation in the first example.

An example of the signal processing and the operation processing of this gas analyzer will be described below using a flowchart of FIG. 3. A signal from the light receiving section 8 that receives light having passed through the inside of the sample cell 2 is inputted into the first signal processing section 18 and the second signal processing section 20, to be subjected to predetermined processing (Step S1). In the first signal processing section 18, the signal intensity Signal($v_0$) with the frequency 2×fa for the harmonic synchronous detection method is extracted, and in the second signal processing section 20, the signal intensity I($v_0$) with a frequency smaller than the frequency fa for the direct absorption spectrometry is extracted. The signal intensities extracted in these signal processing sections 18, 20 are captured into the operation section 22 (Step S2).

In the operation section 22, the switching means 25 captures the reference light intensity signal $I_0(v_0)$ from the reference light intensity signal $I_0(v_0)$ holding section 23-3, and calculates $\ln(I_0(v_0)/I(v_0))$ or $(I_0(v_0)-I(v_0))/I_0(v_0)$ by use of the signal intensity Signal($v_0$) captured from the first signal processing section 18 and I($v_0$) captured from the second signal processing section 20 (Step S3). The switching means 25 decides which is to be outputted, a result of calculation of the molecular number density c of the component to be measured which is obtained by the first operation means 23-1 by the harmonic synchronous detection method by use of Formula (10), or a result of calculation of the molecular number density c of the component to be measured which was obtained by the second operation means 23-2 by the direct absorption spectrometry by use of Formula (7) (Step S4).

As an example of determination by the switching means 25, when $\ln(I_0(v_0)/I(v_0))$ or $(I_0(v_0)-I(v_0))/I_0(v_0)$ is smaller than a previously set threshold value, the result of calculation of the molecular number density c of the component to be measured which was obtained by the first operation means 23-1 by the harmonic synchronous detection method by use of Formula (11) is outputted, with the molecular number density of the component to be measured being regarded as a low molecular number density that can be measured by the harmonic synchronous detection method (Step S5). On the contrary, when $\ln(I_0(v_0)/I(v_0))$ or $(I_0(v_0)-I(v_0))/I_0(v_0)$ is not smaller than the previously set threshold value, the result of calculation of the molecular number density c of the component to be measured which is obtained by the second operation means 23-2 by the direct absorption spectrometry is outputted, with the molecular number density of the component to be measured being regarded as a higher molecular number density than a molecular number density that can be applied with the harmonic synchronous detection method (Step S6).

It is to be noted that, other than the above determination method, the method for determining which is to be used, the harmonic synchronous detection method or the direct absorption spectrometry, may be a determination method where $(I_0(v_0)-I(v_0))$ is compared with a previously set threshold value, and uses the harmonic synchronous detection method in the case of the value being smaller than the threshold value, while using the direct absorption spectrometry in the case of the value being not smaller than the threshold value.

Although both the first operation means 23-1 and the second operation means 23-2 execute the operation processing and a result of the operation, selected by the switching means 25, is outputted in the present example, only the operation means selected by the switching means 25 may execute the operation processing to calculate a molecular number density and make an output, while the nonselected operation means may not execute the operation processing. In that case, there is an advantage of the operation section 22 having a small load.

Example 2

Next, a second example will be described using FIGS. 4A to 4F. A configuration of the entire device of the gas analyzer of the present example is similar to that of FIG. 1, but in the present example, a signal processing system is partially different since a light frequency of laser light is scanned. Hereinafter, a description will be provided with a focus on a different portion from the first example.

In the present example, a drive current of the wavelength tunable laser 6 is changed by means of, for example, a sawtooth wave with a frequency fb that is lower than the frequency fa, thereby scanning an oscillating frequency of laser light. Since the oscillating frequency of laser light is scanned, it is not necessary to highly accurately set the oscillating frequency of laser light to a center frequency of an absorption line of the component to be measured as in Example 1, and since scanning can be continuously performed any number of times, it is possible to improve an S/N ratio by striking an average value of signals. Further, since the light frequency of laser light is scanned to allow measurement of a signal intensity of the light receiving section 8 at the time of the light frequency of laser light being a frequency at which the light is not absorbed by the component to be measured, based on those signal intensities, it is possible to calculate a signal intensity at the time of the frequency of laser light being the center frequency of the absorption line of the component to be measured as a predicted value of the reference light intensity signal $I_0(v_0)$ in the state of nonexistence of the component to be measured, and it is not necessary to previously measure the reference light intensity signal $I_0(v_0)$ as in Example 1.

In the present example, other than the offset direct current voltage generating section 24, the light source driving section 12 is further provided with a laser wavelength scanning voltage generating section 25 that generates a voltage for scanning a sawtooth wave with a cycle of the frequency fb for generating a laser wavelength scanning current, and is configured such that the sawtooth wave scanning voltage is added by an adder 27 to a voltage signal from the offset direct current voltage generating section 24. A signal 24S generated from the offset direct current voltage generating section 24, a signal 25S generated from the laser wavelength scanning voltage generating section 25, and a signal 27S formed by addition of those signals are signals in waveforms shown in FIG. 4c.

In addition to the low-pass filter (LPF) 50 and the A/D converter (ADC2) 52, the second signal processing section 20a is added with a band-pass filter (BPF3) 54 having a transmission region for extracting a signal in the vicinity of the frequency fb, and an A/D converter 56 (ADC3). The low pass filter (LPF) 50 and the A/D converter (ADC2) 52 are ones which extract the signal intensity $I(v_0)$ of the absorption peak as the direct current component signal as in the first example. The band-pass filter (BPF3) 54 is one appropriate for measuring an absorption spectrum that appears in the cycle of the frequency fb, and a signal extracted in the band pass filter (BPF3) 54 is converted to a digital signal by the A/D converter 56 and captured into an operation section 22a. The operation section 22a is realized by a computer.

In a first signal processing section 18a, a low-pass filter (LPF2) 46a needs to extract a signal in the vicinity of the frequency fb unlike the low pass filter (LPF1) 46 of the first example, and thereby has a cutoff frequency of the order of several kHz.

A first operation means 23-1a in the operation section 22a extracts the signal intensity $Signal(v_0)$ based on a scanned signal from the first signal processing section 18a, and calculates the molecular number density c of the component to be measured by the harmonic synchronous detection method by use of foregoing Formula (11) based on the extracted Signal intensity $(v_0)$ and $I_0(v_0)$ extracted by a second operation means 23-2a. The second operation means 23-2a extracts the signal intensities $I(v_0)$ and $I_0(v_0)$ from two scanned signals from the second signal processing section 20a, and calculates the molecular number density c of the component to be measured by the direct absorption spectrometry by use of foregoing Formula (7) based on the extracted signal intensities $I(v_0)$ and $I_0(v_0)$. The first operation means 23-1a and the second operation means 23-2a constantly perform operations, and the switching means 25 decides which is to be outputted, the molecular number density c as a result of the operation of the first operation means 23-1a or that of the second operation means 23-2a, based on the signal intensities $I(v_0)$ and $I_0(v_0)$ from the first operation means 23-1a.

An operation of the present example will be described.

In the adder 26, a signal 39S with the modulation frequency fa is added to a sawtooth signal 27S with the frequency fb from the adder 27, to give a drive signal 26S as shown in FIG. 4D, which is applied to the voltage/current converter 28. Laser oscillation is controlled by this drive signal, and hence, generated laser light is one which is a sawtooth wave with the frequency fb, has a wavelength scanned with an oscillating frequency $v_0$ at the center, and is modulated with the frequency fa. The frequency fb is well lower than the frequency fa, and preferably from several Hz to several hundreds of Hz. The modulation frequency fa is generally on the order of several kHz to several MHz. As thusly described, the sample gas is irradiated with laser light added with a sine wave modulated with the frequency fa. Herein, it is desirable that an amplitude of the sine wave with the frequency fa be sufficiently smaller than an amplitude of the sawtooth wave with the frequency fb. This is because, as in Example 1, if the above amplitude is excessively large, an influence of a component with another light frequency strongly appears in the signal intensity $I(v_0)$ detected in the second signal processing section 20a, making precise measurement impossible.

Laser light absorbed by the component to be measured in the sample cell is detected in the photodiode 40 of the light receiving section 8, and subjected to signal processing in the first signal processing section 18a and the second signal processing section 20a.

The signals extracted by the low-pass filter 50 and the band-pass filter 54 in the second signal processing section 20a respectively become signals shown as signals 50S, 54S in FIG. 4D. The signal 50S corresponds to the signal intensity $I(v_0)$, and this is the same as in the case of the first example. The signal 54S is a signal that repeatedly appears at the frequency fb. These signals are digital-converted by the respective A/D converters 52, 56, captured into the operation section 22a and added to each other, to give a signal shown as a signal (50S+54S) in FIG. 4D.

In the first signal processing section 18a, in the harmonic synchronous detection section 44, the detection signal 42S from the light receiving section 8 is multiplied by the clock signal with the frequency 2fa from the 2fa clock generating section 30 of the modulation section 16, the half of the waveform of the frequency 2fa is reversed, and the frequency components other than the frequency 2fa are removed, to obtain a signal 44S. Passing of this signal 44S through a low-pass filter 46a leads to extraction of a signal 46aS including the peak signal intensity $Signal(v_0)$ with a harmonic component of the frequency 2fa. Those signals 42S, 44S and 46aS have waveforms as shown in FIG. 4E. The synchronous detection is performed at the frequency 2fa as in the first example, but in the present example, since a wave number v of laser light is scanned, a signal having passed through the low-pass filter 46a appears as having a waveform of the cycle of the frequency fb. The signal 46aS is converted to a digital signal in the A/D converter 48, and thereafter captured into the operation section 22a.

Figure 4A:
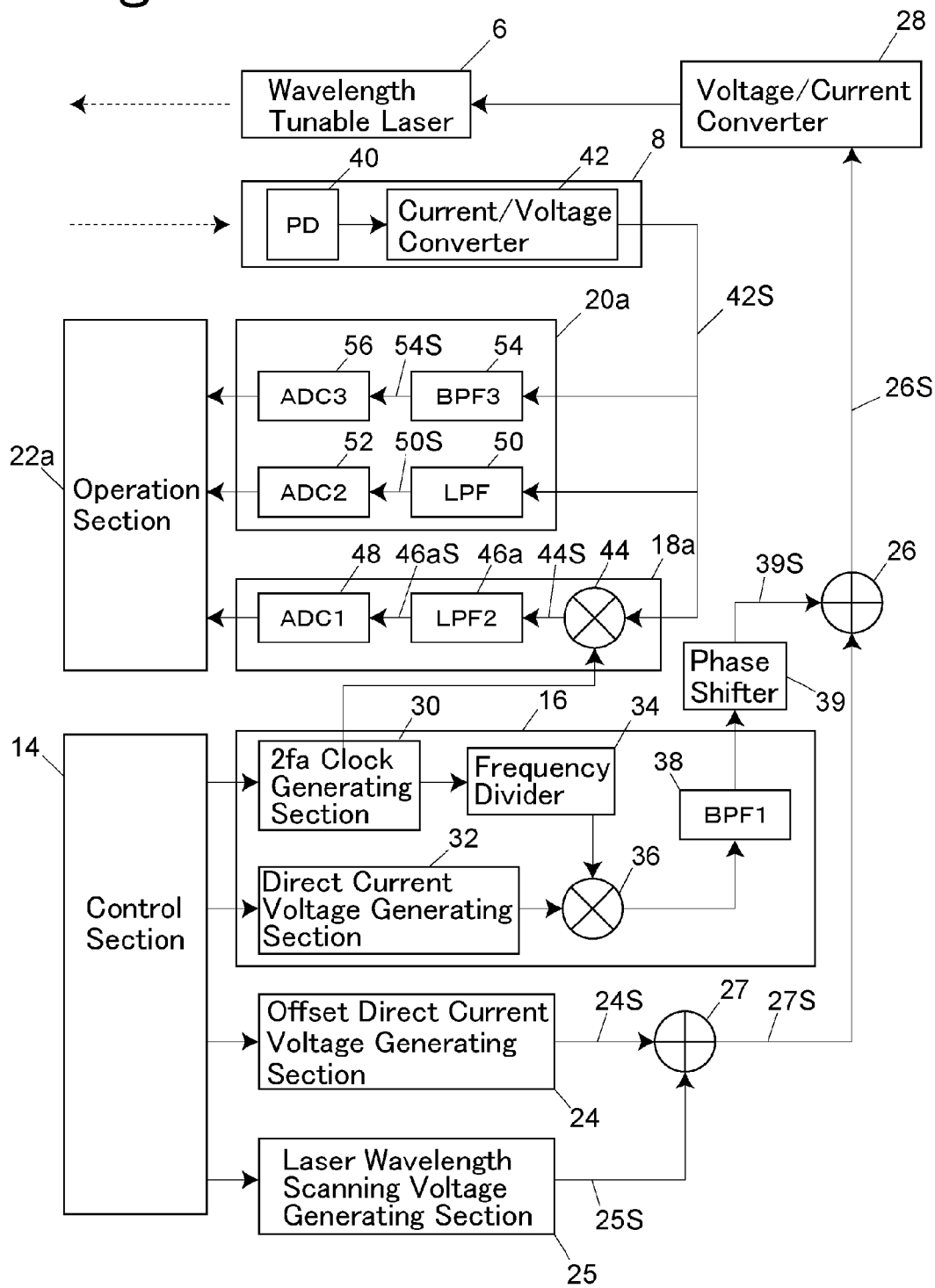
FIG. 4A is a block diagram showing a second example.
Figure 4B:
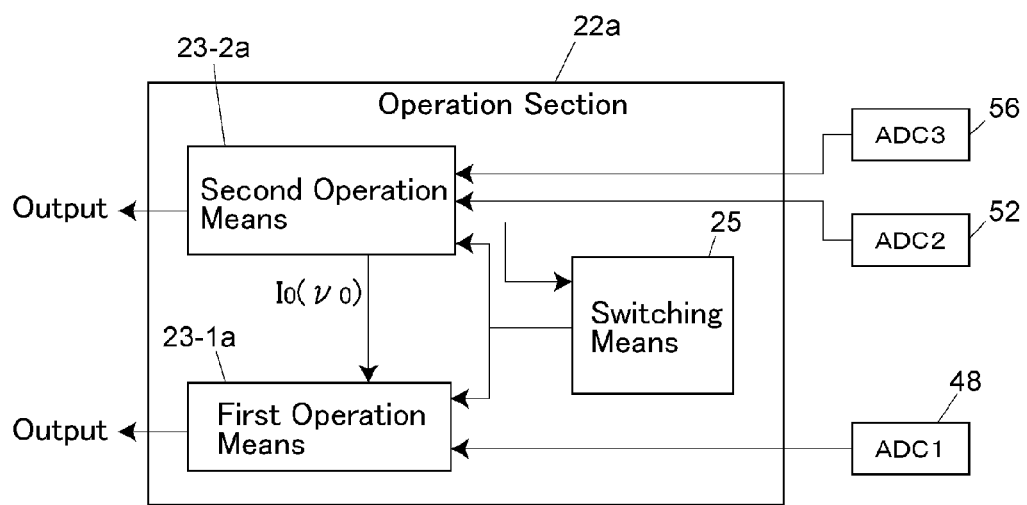
FIG. 4B is a block diagram showing an operation section according to the second example.
Figure 4C:
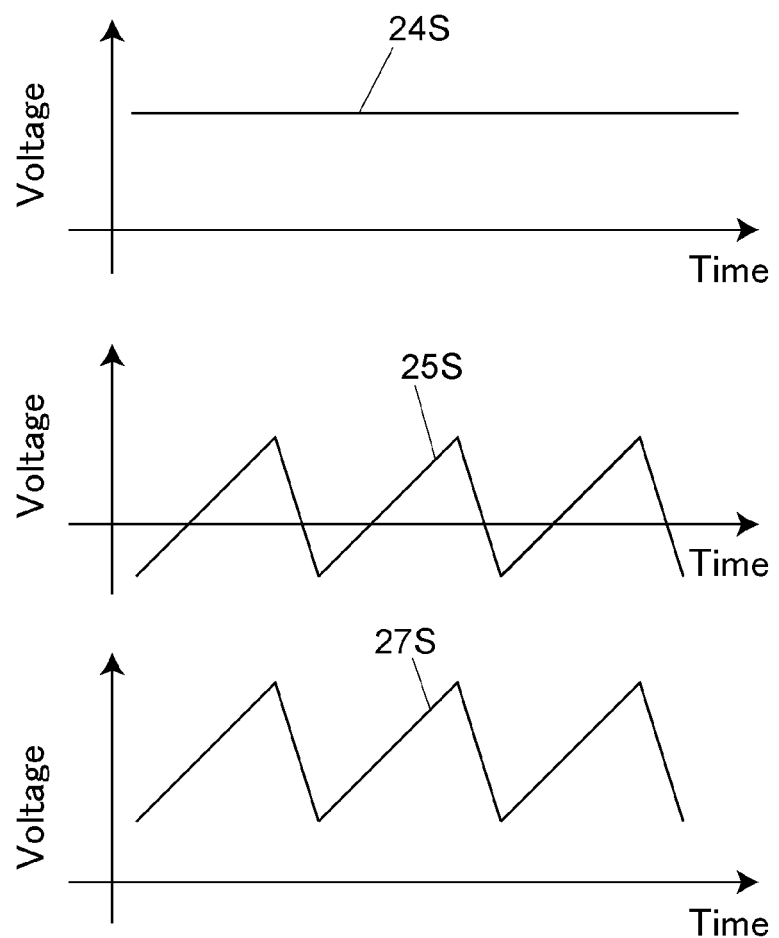
Figure 4F:
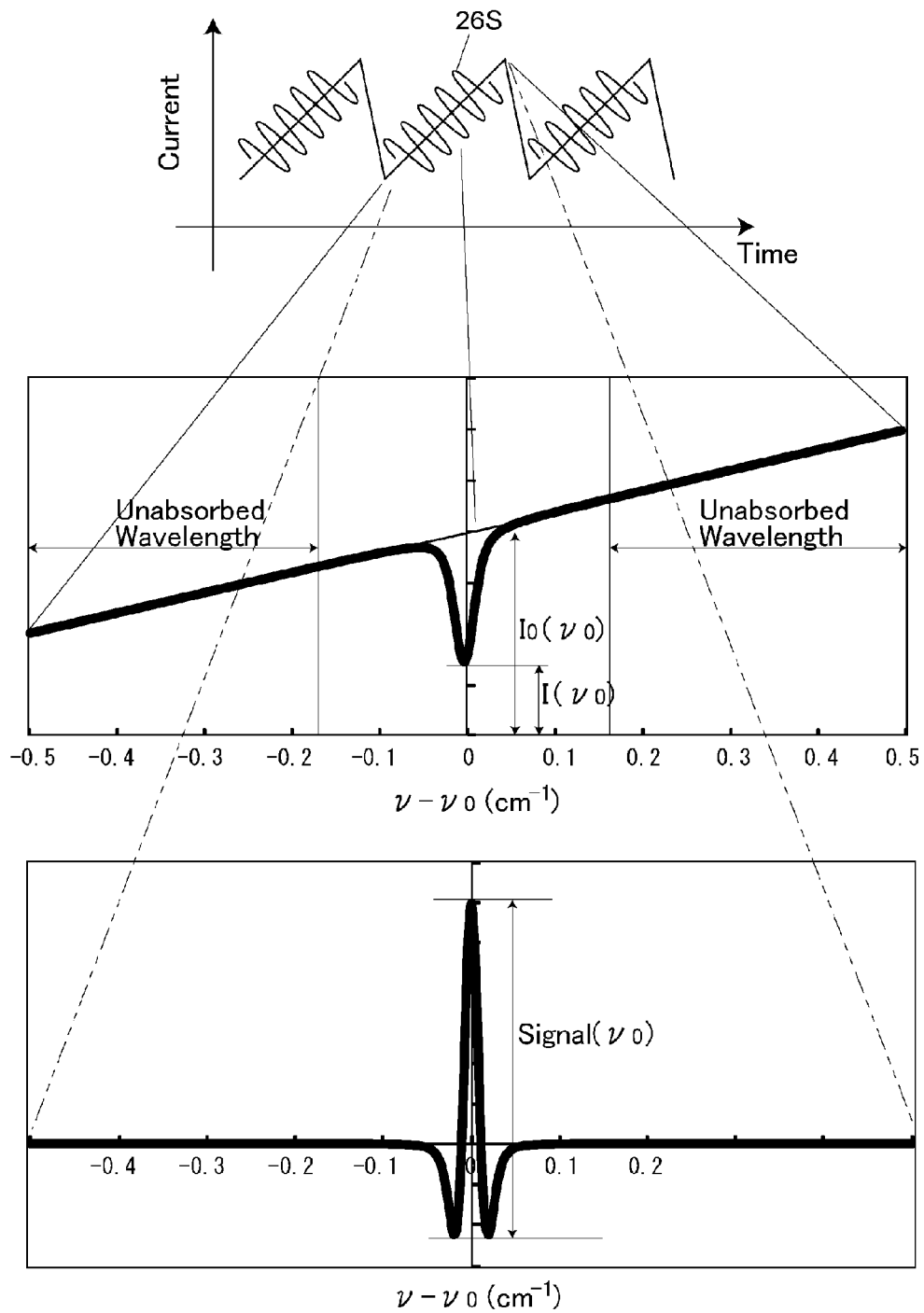
Figure 5:
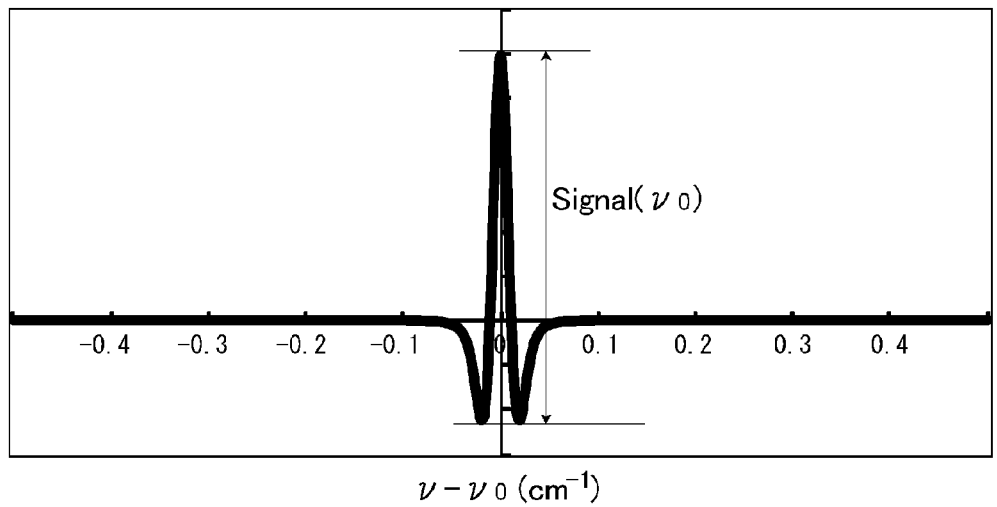
FIG. 5 is an example of a light detection signal extracted by the first signal processing section in the second example.
Figure 6:
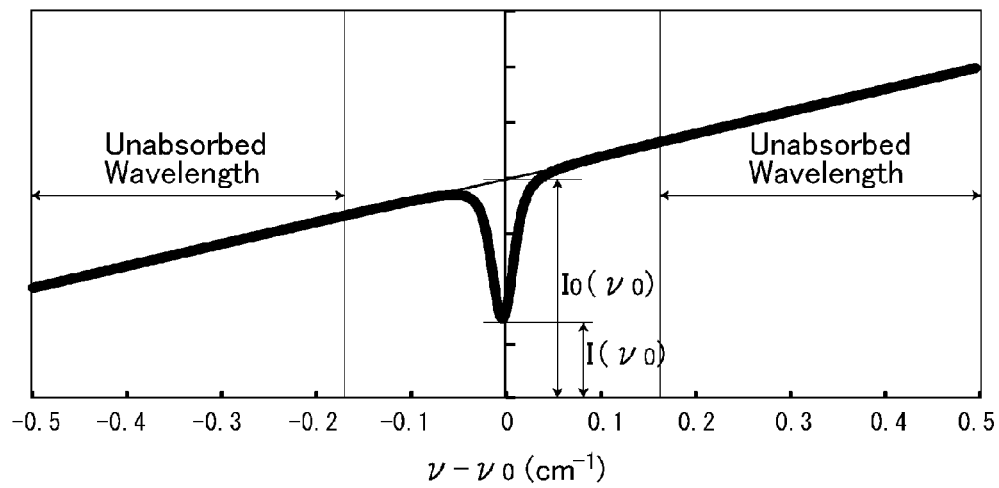
FIG. 6 is an example of a light detection signal extracted by the second signal processing section in the second example.

FIG. 5 is an example of a waveform of a signal extracted by the first signal processing section 18a, and FIG. 6 is an example of a waveform of a signal extracted by the second signal processing section 20a. In FIGS. 5 and 6, a horizontal axis indicates a difference $(v-v_0)$ between the light frequency v of laser light and the center frequency $v_0$ of the absorption line of the component to be measured as a wave number, and a vertical axis indicates a detection signal intensity. When the relation with the signal 26S for scanning a laser wavelength is shown, these signals are repeatedly obtained by the cycle of the frequency fb of a sawtooth wave, as shown in FIG. 4F. As thusly described, it is possible to repeatedly obtain signals in waveforms as shown in FIGS. 5 and 6 in the cycle of the frequency fb, so as to enhance an S/N ratio by means of averaging processing.

As shown in FIG. 5, the first operation means 23-1a in the operation section 22a extracts the signal intensity $Signal(v_0)$ as a height from a lower peak to an upper peak in the waveform of the signal extracted by the signal processing section 1.

On the other hand, the second operation means 23-2a in the operation section 22a extracts $I(v_0)$ as a signal intensity in the center frequency of the absorption line of the component to be measured in FIG. 6, and creates an approximate line based on a signal intensity around this waveform, thereby to extract the reference light intensity signal $I_0(v_0)$. Hence, it is possible to obtain all of $I_0(v_0)$, $I(v_0)$ and $Signal(v_0)$ by onetime measurement which is performed by scanning a frequency of laser light. The operation processing for the molecular number density c of the component to be measured based on $I_0(v_0)$, $I(v_0)$ and $Signal(v_0)$ is the same as in the first example.

The switching means 25 captures the signals $I_0(v_0)$ and $I(v_0)$ from the second operation means 23-2a and decides, from a similar determination to that in the first example, which is to be outputted, a result of the operation of the molecular number density by the first operation means 23-1*a* or that by the second operation means 23-2*a*. In this case, the operation of the molecular number density c from the signal intensity Signal($v_0$) by the first operation means 23-1*a* and the operation of the molecular number density c from the signals $I_0(v_0)$ and $I(v_0)$ by the second operation means 23-2*a* are constantly executed, and a result of the operation of the molecular number density is outputted when selected from the switching means 25.

Also in the case of the present example, the second signal processing section 20*a* may include one low-pass filter 50 and one A/D converter 52. However, in that case, the low-pass filter 50 needs to allow the laser wavelength scanning frequency fb to pass therethrough, and hence, it needs to be a low-pass filter having a cutoff frequency of the order of several kHz.

Figure 7:
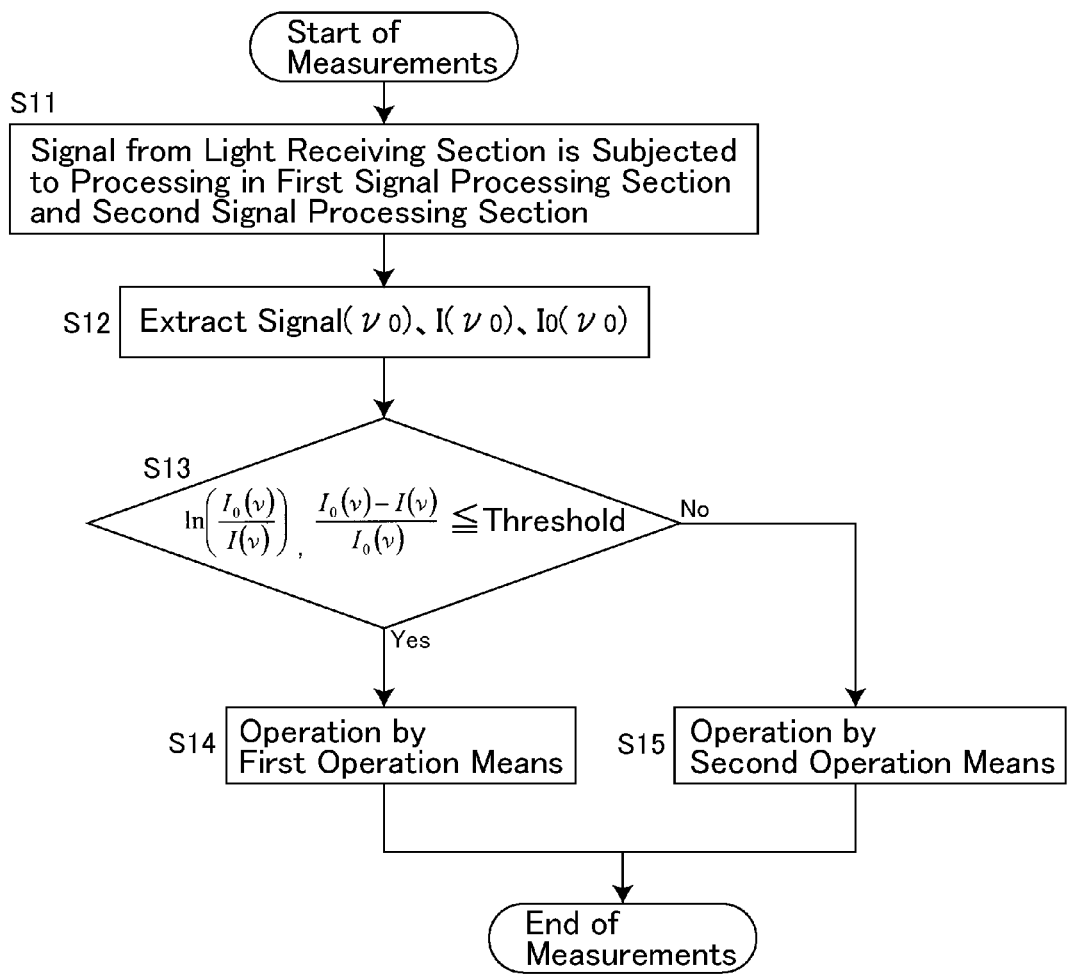
FIG. 7 is a flowchart showing a signal processing operation and an operation processing operation in the second example.

An example of the signal processing and the operation processing of the gas analyzer in the present example will be described below using a flowchart of FIG. 7. A signal from the light receiving section 8 that receives light having passed through the inside of the sample cell 2 is inputted into the first signal processing section 18*a* and the second signal processing section 20*a*, to be subjected to predetermined processing, and data showing the waveforms shown in FIGS. 5 and 6 are inputted into the operation section 22*a* (Step S11). The signal intensity Signal($v_0$) is extracted in the first operation means 23-1*a*, and the signals $I(v_0)$ and $I_0(v_0)$ are extracted in the second operation means 23-2*a* (Step S12).

In the operation section 22*a*, the switching means 25 calculates $\ln(I_0(v_0)/I(v_0))$ or $(I_0(v_0)-I(v_0))/I_0(v_0)$ by use of the signals $I(v_0)$ and $I_0(v_0)$ from the second operation means 23-2*a*, and based on results of the calculation, the operation section 22*a* decides which is to be outputted, the result of the operation of the molecular number density is to be outputted by the first operation means 23-1*a* or that by the second operation means 23-2*a* (Step S13). When the switching means 25 specifies the first operation means 23-1*a*, the switching means 25 outputs the molecular number density c of the component to be measured which is calculated by the first operation means 23-1*a* by the harmonic synchronous detection method by use of Formula (11) (Step S14), and when the switching means 25 specifies the second operation means 23-2*a*, the switching means 25 outputs the molecular number density c of the component to be measured which is calculated by the second operation means 23-2*a* by the direct absorption spectrometry by use of Formula (1) (Step S15).

Example 3

Figure 8A:
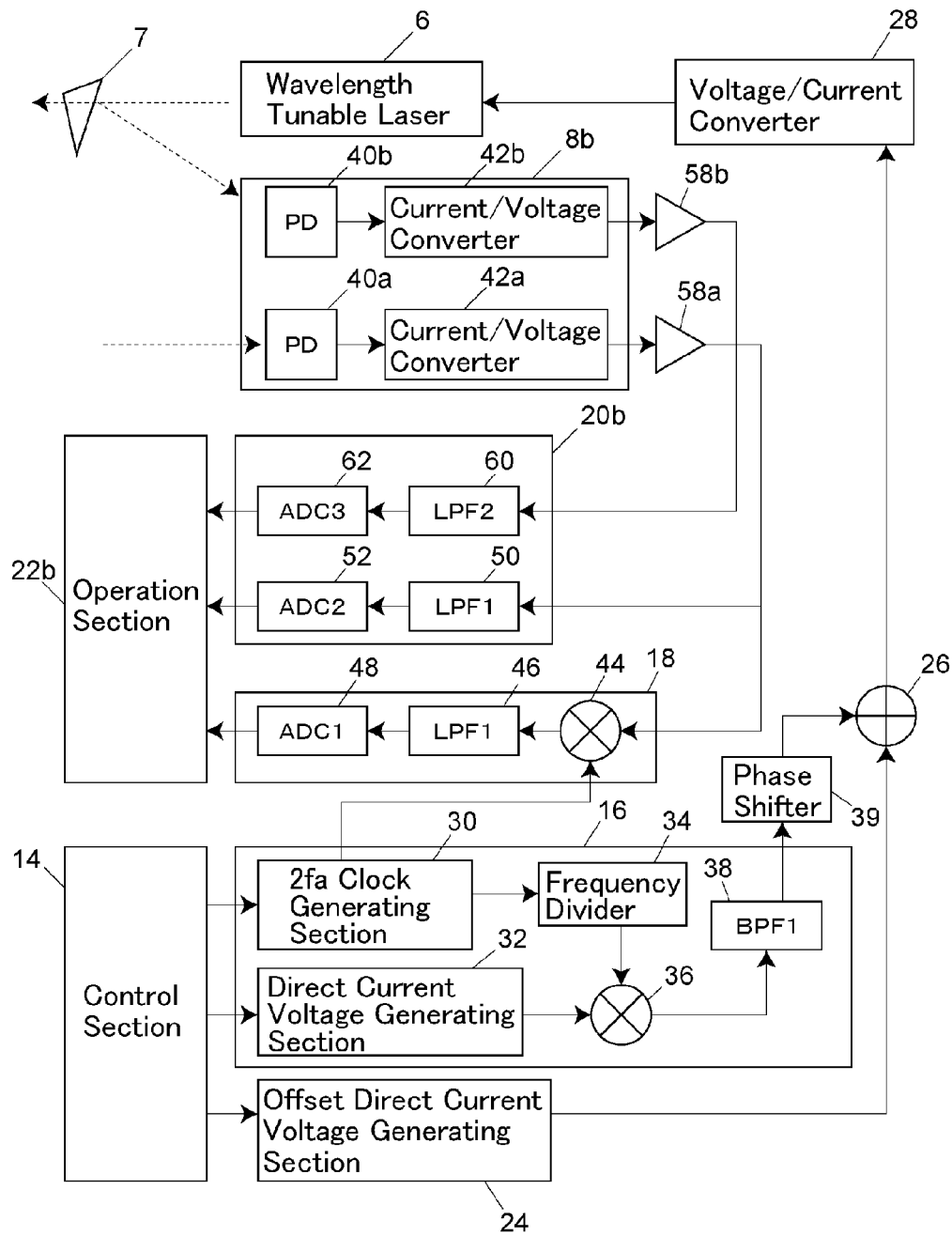
FIG. 8A is a block diagram showing a third example.
Figure 8B:
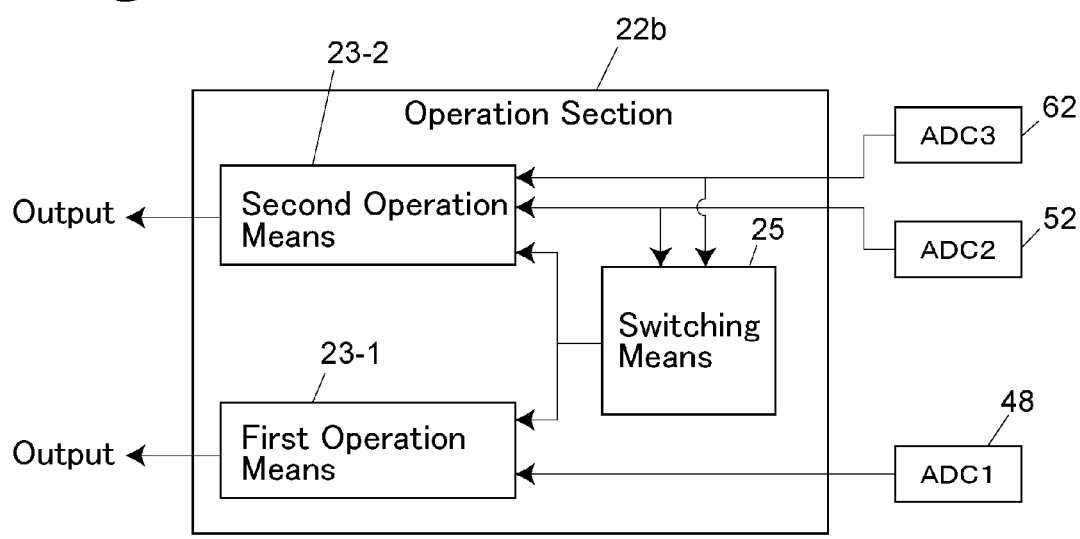
FIG. 8B is a block diagram showing an operation section according to the third example.

Next, a third example of the gas analyzer will be described using FIGS. 8A and 8B. In the present example, it is configured such that part of laser light emitted from the wavelength tunable laser 6 is split from laser light, with which the sample cell 2 is irradiated, by a beam splitter 7 and the split light is then led to a light receiving section 8*b* side without being allowed to pass through the sample cell 2. In addition to a photodiode 40*a* for detecting laser light allowed to pass through the inside of the sample cell 2 and a current/voltage converter 42*a* that converts a current signal of the photodiode 40*a* to a voltage signal, the light receiving section 8*b* is provided with a photodiode 40*b* for detecting laser light not allowed to pass through the inside of the sample cell 2 and a current/voltage converter 42*b*, and simultaneously detects the laser light allowed to pass through the inside of the sample cell 2 and the laser light not allowed to pass therethrough in separate detectors. In the photodiode 40*b*, for detecting the laser light not allowed to pass through the inside of the sample cell 2, its detection signal is used as a detection signal in the case of no absorption by the component to be measured, namely as a reference light intensity signal.

In addition to the low-pass filter (LPF1) 50 and the A/D converter (ADC2) 52 for processing a signal from the photodiode 40*a*, the second signal processing section 20*b* is provided with a low-pass filter (LPF2) 60 and an A/D converter (ADC3) 62 for processing a signal from the photodiode 40*b*. The current/voltage converter 42*a* is connected to the low-pass filter (LPF1) 50 via an amplifier 58*a*, and the current/voltage converter 42*b* is connected to the low-pass filter (LPF2) 60 via an amplifier 58*b*. The amplifiers 58*a*, 58*b* are ones for performing adjustment such that an influence of attenuation or the like at the time of reflection of laser light on the reflectors 10*a*, 10*b* is eliminated and signals from the photodiodes 40*a*, 40*b* can be compared with each other as equivalent signals.

Although other configurations are similar to the configuration of the first example shown in FIGS. 2A and 2B, the reference light intensity signal $I_0(v_0)$ is obtained as a signal from the photodiode 40*b*, thereby eliminating the need for providing the operation section 22*b* with the $I_0(v_0)$ holding section that holds the reference light intensity signal $I_0(v_0)$. The operation section 22*b* is realized by a computer.

With this configuration, Signal($v_0$) is extracted in the first signal processing section 18 and $I(v_0)$ and $I_0(v_0)$ are extracted in the second signal processing section 20*b*, and in the operation section 22*b*, as in the first example, calculation of the molecular number density c of the component to be measured by the harmonic synchronous detection method and calculation of the molecular number density c of the component to be measured by the direct absorption spectrometry are performed, followed by switching and outputting by the switching means 25.

Although the above examples are ones obtained by applying the gas analyzer according to the present invention to measurement of the molecular number density of moisture in the component to be measured, the present invention is applicable to measurement of a molecular number density of an arbitrary gas other than moisture.

The invention claimed is:

1. A gas analyzer, comprising:
   a sample cell for allowing a sample gas to flow therethrough;
   a laser irradiation section for irradiating the sample cell with laser light with a specific light frequency which is absorbed by a component to be measured in the sample gas;
   a light source driving section for applying a drive current for generating the laser light to the laser irradiation section;
   a modulation section for modulating the drive current applied from the light source driving section to the laser irradiation section with a modulation frequency of a first frequency fa;
   a light receiving section for receiving the laser light having passed through the inside of the sample cell;
   a first signal processing section for detecting a harmonic signal intensity Signal(v) by a harmonic synchronous detection method by synchronously detecting a light detection signal of the light receiving section at a frequency being an integral multiple of the modulation frequency;
   a second signal processing section for detecting a light intensity signal I(v) at the specific light frequency by capturing a light detection signal of the light receiving section not through the first signal processing section, and by cutting off a frequency component not smaller than the first frequency fa by means of a frequency filter; and an operation section for capturing the harmonic signal intensity Signal (ν) detected in the first signal processing section and the light intensity signal I(ν) detected in the second signal processing section, to calculate a molecular number density c of the component to be measured in the sample gas, wherein the operation section includes a first operation means for calculating the molecular number density c of the component to be measured in the sample gas from the harmonic signal intensity Signal(ν) and a reference light intensity signal $I_0(\nu)$, the reference light intensity signal being $I_0(\nu)$ when the laser light is not absorbed by the component to be measured at the specific light frequency, and a second operation means for calculating the molecular number density c of the component to be measured in the sample gas from the light intensity signal I(ν) and the reference light intensity signal $I_0(\nu)$ by direct absorption spectrometry.

2. The gas analyzer according to claim 1, wherein the operation section includes switching means, and the switching means is configured to determine from the light intensity signal I(ν) and the reference light intensity signal $I_0(\nu)$ as to whether the molecular number density of the component to be measured in the sample is a low molecular number density which is suitable for measurement by the harmonic synchronous detection method, or a molecular number density which is higher than the above molecular number density, and thus suitable for measurement by the direct absorption spectrometry, and the switching means is configured to switch an output so as to output the molecular number density c calculated by the first operation means at the time of obtaining a determination result that the molecular number density is the molecular number density suitable for the measurement by the harmonic synchronous detection method, and to output the molecular number density c calculated by the second operation means at the time of obtaining a determination result that the molecular number density is the molecular number density suitable for the measurement by the direct absorption spectrum.

3. The gas analyzer according to claim 2, wherein the switching means is configured to obtain a determination result that the molecular number density is a low molecular number density suitable for the measurement by the harmonic synchronous detection method at the time of $\ln(I_0(\nu)/I(\nu))$ or $(I_0(\nu)-I(\nu))/I_0(\nu)$ being not higher than a previously set value, and to obtain a determination result that the molecular number density is a molecular number density suitable for the measurement by the direct absorption spectrum at the time of the above value being larger than the previously set value.

4. The gas analyzer according to claim 2, wherein the switching means is configured to obtain a determination result that the molecular number density is a molecular number density suitable for the measurement by the harmonic synchronous detection method at the time of a difference between the light intensity signal I(ν) and the reference light intensity signal $I_0(\nu)$ being smaller than a previously set threshold, and to obtain a determination result that the molecular number density is a molecular number density suitable for the measurement by the direct absorption spectrum at the time of the above difference being larger than the set value.

5. The gas analyzer according to claim 1, wherein the light source driving section is configured to set a drive current to be applied to the laser irradiation section such that a frequency of laser light applied from the laser irradiation section becomes the specific light frequency, the operation section includes a reference light intensity signal $I_0(\nu)$ holding section for holding the reference light intensity signal $I_0(\nu)$ at the time of no absorption of laser light by the component to be measured at the specific light frequency, and the first operation means and the second operation means are configured to use, as the reference light intensity signal $I_0(\nu)$, a value of the reference light intensity signal $I_0(\nu)$ held in the reference light intensity signal $I_0(\nu)$ holding section.

6. The gas analyzer according to claim 1, wherein the specific frequency is a center frequency $(\nu_0)$ of an absorption line of the component to be measured.

7. The gas analyzer according to claim 1, further comprising a laser wavelength scanning current generating section for changing a laser drive current to be applied to the laser irradiation section such that the laser irradiation section oscillates even laser light with such a light frequency as not to be absorbed by the component to be measured, wherein the second signal processing section includes a portion for measuring a transmitted light intensity at such a frequency so as not to be absorbed by the component to be measured at the time when the laser wavelength scanning current generating section oscillates the laser light with such a light frequency as not to be absorbed, to approximately calculate from a result of the measurement the reference light intensity signal $I_0(\nu)$ at the specific light frequency corresponding to the case of no absorption of light by the component to be measured.

8. The gas analyzer according to claim 7, wherein the laser wavelength scanning current generating section is configured to generate a sawtooth wave with a cycle of a second frequency fb that is lower than the first frequency fa.

9. The gas analyzer according to claim 1, further comprising:

a beam splitter for splitting a laser light emitted from the laser irradiation section into a laser light to be incident into the sample cell and a laser light not to be incident into the sample cell; and a reference light receiving section for receiving the laser light that is the one split by the beam splitter and not incident into the sample cell, wherein the second signal processing section includes a part for cutting off a component not smaller than the first frequency fa component in a detection signal detected by the reference light receiving section by means of a frequency filter, and for detecting a light intensity at the specific light frequency which has appeared after the above process, to regard the light intensity as the reference light intensity signal $I_0(\nu)$ at the specific light frequency which corresponds to the case of no absorption of light by the component to be measured.

* * * * *